United States Patent
Murray et al.

(10) Patent No.: US 6,492,568 B1
(45) Date of Patent: Dec. 10, 2002

(54) REMOVAL OF PHOSPHORUS-CONTAINING COMPOUNDS FROM AN OLEFIN FEEDSTOCK

(75) Inventors: Brendan Dermot Murray, Houston, TX (US); Zaida Diaz, Houston, TX (US); Glenn Charles Komplin, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/566,463

(22) Filed: May 8, 2000

(51) Int. Cl.[7] .................. C07C 27/20; C07C 27/22; C07C 27/24; C07C 29/15
(52) U.S. Cl. ............................................. 568/909
(58) Field of Search ................. 568/909; 585/823, 585/329, 512

(56) References Cited

U.S. PATENT DOCUMENTS

| | | |
|---|---|---|
| 3,674,886 A | 7/1972 | Komatsu et al. |
| 3,676,523 A | 7/1972 | Mason |
| 3,686,351 A | 8/1972 | Mason |
| 3,737,475 A | 6/1973 | Mason |
| 3,770,619 A | 11/1973 | Derrien et al. |
| 4,020,121 A | 4/1977 | Kister et al. |
| 4,076,842 A | 2/1978 | Plank et al. |
| 4,351,980 A | 9/1982 | Reusser et al. |
| 4,551,443 A | 11/1985 | Hudson |
| 4,717,785 A  * | 1/1988 | Paxson ....................... 585/823 |
| 5,072,057 A | 12/1991 | Oswald et al. |
| 5,112,519 A | 5/1992 | Giacobbe et al. |
| 5,376,393 A | 12/1994 | Nardelli |
| 5,378,439 A | 1/1995 | Delobel et al. .............. 423/210 |
| 5,510,306 A | 4/1996 | Murray ........................ 502/64 |
| 5,780,694 A  * | 7/1998 | Singleton ..................... 568/909 |
| 5,849,960 A  * | 12/1998 | Singleton et al. ........... 568/909 |
| 6,084,140 A | 7/2000 | Kitamura et al. |

FOREIGN PATENT DOCUMENTS

EP   0 903 333 A1   3/1999

OTHER PUBLICATIONS

Research Disclosure, Kenneth Mason Publications, Hampshire, GB, No. 415, Nov. 1998, pp. 1445–1451, XP000824939.*

"Sasol Detergent Alcohols", Preliminary Sasol R&D Technical Bulletin; Oct. 1995.

"Verfahren Zur Katalytischen Oligomerisierung Von Monoolefinen" Research Disclosure, Kenneth Mason Publications, Hampshire, GB, No. 415, Nov. 1998, pp. 1445–1451, XP000824939.

Verfarhren Zur Katalytishen Oligomerisierung Von Monoolefinen Research Disclosure, Kenneth Mason Publications, Hampshire, GB, No. 415, Nov. 1998, pp. 1445–1451, XP000824939.

* cited by examiner

*Primary Examiner*—Samuel Barts
*Assistant Examiner*—Elvis O. Price

(57) ABSTRACT

The invention pertains to a process of removing phosphorus-containing impurities from an olefin stream using a sorbent comprising a metal. The olefin stream preferably comprises primarily olefins having at least 6 carbon atoms.

52 Claims, No Drawings

REMOVAL OF PHOSPHORUS-CONTAINING COMPOUNDS FROM AN OLEFIN FEEDSTOCK

FIELD OF THE INVENTION

The invention pertains to a process of removing contaminants from olefin feedstocks using a sorbent comprising a metal. The contaminants removed preferably are phosphorus-containing compounds, most preferably organophosphines and/or organophosphine oxides. Preferred olefin feedstocks are made by oligomerizing ethylene to linear olefins having from about 6 to about 36 carbon atoms, preferably from about 11 to about 20 carbon atoms, and most preferably from about 14 to about 18 carbon atoms.

BACKGROUND OF THE INVENTION

Depending upon the method of their production, olefin feedstocks may comprise a variety of impurities. Impurities found in olefins that are produced by oligomerization of ethylene units include phosphorus-containing impurities, including but not necessarily limited to organophosphines and organophosphine oxides. These phosphorus-containing compounds are largely removed from many olefin streams during the process of distillation to separate various "cuts" of olefins. Unfortunately, the organophosphines and organophosphine oxides found in $C_{14}$–$C_{18}$ streams tend to co-distill with the $C_{14}$–$C_{18}$ in the product, making it difficult, if not impossible to remove these phosphine impurities by simple distillation.

$C_6$–$C_{36}$ olefins have utility in the fields of paper and pulp processing, drilling fluids, and machine or metal working oils. Alcohols of such olefins have commercial importance in a variety of applications, including detergents, soaps, surfactants, and freeze point depressants in lubricating oils. These alcohols are produced by a number of commercial processes, such as by oxo or hydroformylation of long chain olefins. In many of these applications, the olefin feedstocks are treated using acid catalysts.

Unfortunately, any phosphorus-containing compounds in these olefin feedstocks will negatively affect acid catalysts. The phosphorus-containing moieties are basic in nature and will neutralize the active acid sites of the catalyst, which lowers catalyst activity and performance. The organophosphine moeities may even cause the olefins to oligomerize into undesirable forms.

Methods are needed to reduce the phosphorus-content of olefin feedstocks.

SUMMARY OF THE INVENTION

The present invention provides a method for purifying an olefin feed comprising a content of phosphorus-containing compounds. The method comprises contacting the olefin feed with a sorbent comprising a metal under conditions and for a time effective to reduce the content of phosphorus-containing compounds, producing a purified olefin feed.

DETAILED DESCRIPTION OF THE INVENTION

The present invention provides a process and sorbents which efficiently and effectively reduce the content of phosphorus-containing compounds in olefin streams. In a preferred embodiment, the content is reduced to about 1 ppm or less, preferably about 0.5 ppm or less, most preferably to about 0.1 ppm or less. Given sufficient run time, the sorbents reduce the content of phosphorus-containing compounds in the olefin stream to parts per billion (ppb) levels.

The invention may be used to treat substantially any olefin stream. Preferred olefin streams are linear olefin streams made by oligomerizing ethylene. Some of the known processes for oligomerizing ethylene use organophosphorus compounds that result in phosphorus as a contaminant in the resulting olefin stream. A preferred commercially available olefin feed for the treatment of the present invention is the product marketed in the United States by Shell Chemical Company under the trademark NEODENE®. In a preferred embodiment, the olefin feedstock is treated before exposure to an acid catalyst, or before exposure to other conditions which would be adversely affected by the basic nature of phosphorus-containing contaminants.

In a most preferred embodiment, the olefin stream is the feedstock for the skeletal isomerization catalyst used in the method described in U.S. Pat. No. 5,849,960, which has been incorporated herein by reference. The olefins used in the feed to this skeletal isomerization catalyst are mono-olefins having at least 6 carbon atoms, preferably having from about 11 to about 20 carbon atoms, and most preferably having from about 14 to about 18 carbon atoms.

In general, the olefins in the feed to the skeletal isomerization catalyst are predominately linear. While the olefin feed can contain some branched olefins, the olefin feed processed for skeletal isomerization preferably contains greater than about 50 percent, more preferably greater than about 70 percent, and most preferably greater than about 80 mole percent or more of linear olefin molecules.

The olefin feed to the skeletal isomerization catalyst does not consist of 100% olefins, and usually contains a distribution of mono-olefins having different carbon lengths, with at least 50 wt. % of the olefins being within the stated carbon chain range or digit, however specified. Preferably, the olefin feed will contain greater than 70 wt. %, more preferably about 80 wt. % or more of mono-olefins in a specified carbon number range, the remainder of the product being olefins of other carbon number or carbon structure, diolefins, paraffins, aromatics, and other impurities resulting from the synthesis process. The location of the double bond is not limited. The olefin feed composition may comprise alpha olefins, internal olefins, or a mixture thereof.

The sorbent of the present invention comprises a suitable metal, preferably comprising metal oxide, on a suitable support. Preferred metals are transition metals, including but not necessarily limited to those selected from Groups 3–12 of the Periodic Table of the Elements. When the Periodic Table of the Elements is referred to herein, the source of the Periodic Table is: F. Cotton et al. *Advanced Inorganic Chemistry* (5th Ed. 1988). Suitable metals include, but are not necessarily limited to Sc, V, Cr, Fe, Co, Ni, Cu, Zn, Zr, Nb, Mn, Ag and combinations thereof. Preferred metals are Fe, Co, Ni, Mn, Ag and Cu. In a preferred embodiment, the metal is silver or copper, preferably in the form of oxides. The sorbent suitably comprises from about 0.1 wt. % to about 50 wt. % of the metal oxide of the foregoing metals, preferably copper. Preferably, the sorbent comprises from about 1 wt. % to about 20 wt. %, more preferably from about 5 wt. % to about 15 wt. %, and most preferably from about 8 wt. % to about 10 wt. % of the metal oxide.

The metal oxide resides on a suitable support material. Although the surface area of the support is not a critical feature, the surface area preferably is at least about 10 m²/g in order to provide sufficient contact between the sorbent and the olefin stream. In a preferred embodiment, the support has a surface area of from about 100 m²/g to about 900 m²/g. Acidic supports are more advantageous than basic supports. Suitable support materials are acidic or neutral, most preferably acidic. Suitable support materials include, but are not necessarily limited to alumina, silica, molecular sieves, such as zeolites, activated carbon, aluminosilicate clays, amorphous silicoaluminas, and the like. Where the support material surface is porous, the pores preferably are sufficiently large to permit entry of bulky phosphorus containing compounds in the feed. A most preferred support material for copper is an acidic or neutral alumina. A most preferred support material for silver is X-zeolite. A commercially available sorbent that is suitable for use in the present invention is SELEXSORB AS™, which is commercially available from Alcoa Industrial Chemicals.

It is preferred for the particles of supported sorbent to be as small as possible; however, if the size of the particles is too small, the pressure drop through the bed becomes too large. Very small particles also are difficult to retain in the sorbent bed. SELEXSORB AS™ is purchased in the form of ⅛ inch spheres, and may be used in the process as purchased. However, spheres are not the most efficient particle shape for purposes of maximizing particle surface to volume ratio. Because of this, if SELEXSORB AS™ is used as the sorbent, it is preferred to grind or otherwise reduce the ⅛ inch spheres into the smallest particles possible without inducing an undue pressure drop or loss of sorbent from the sorbent bed. The particles may have substantially any form, including but not necessarily limited to spherical form, tablet form, cylindrical form, multi-lobed cylindrical forms, and their corresponding hollow counterparts. In a preferred embodiment, the particles have a diameter of from about 50 mesh to about 6 mm, preferably about 0.8 mm (1/32 inch) to about 1.6 mm (1/16 inch), most preferably about 0.8 mm. The length of the particles is not critical, with suitable lengths including, but not necessarily limited to less than about 10 mm, preferably from about 3 mm to about 5 mm.

In a preferred embodiment, the support material is an alumina extrudate which is extruded as a paste using an acidic or neutral alumina powder. The "paste" is extruded or otherwise molded into a multilobed cylindrical form. The resulting material preferably is dried at temperatures of at least about 100° C. and calcined at about 500° C. or more in the presence of flowing air in a muffle furnace or purged high temperature air drier or rotary calciner. The copper oxide may be deposited onto the support using any suitable technique, including but not necessarily limited to ion exchange, co-mulling, or impregnation. A preferred technique is pore volume impregnation using a solution of a copper salt, such as copper nitrate, copper carbonate, or other suitable salts. Although the following illustration uses a copper nitrate solution, the use of other Cu salt solutions may produce a more uniform Cu loading. Copper nitrate is very soluble in water, and tends to wick out of the pores during drying. The result may be more CuO on the outside of the pellets, although smaller pellets are less prone to this effect.

Persons of ordinary skill in the art have the knowledge required to calculate how to incorporate a given wt % of CuO or other material onto a sorbent using the foregoing techniques. For example, where 100 g of an alumina has a water pore volume of 83 ml, the following is a formula by which a sorbent containing 9 wt. % CuO is formed:

$$[(9 \text{ g. CuO}/100 \text{ g. final sorbent}) \times$$
$$(1 \text{ mole CuO}/79.54 \text{ g.}) \times [1 \text{ mole Cu (NO}_3)_2 \cdot 2.5 \text{ H}_2\text{O/mole CuO}] \times$$
$$(232.59 \text{ g. Cu (NO}_3)_2 \cdot 2.5 \text{ H}_2\text{O/mole Cu (NO}_3)_2 \cdot 2.5 \text{ H}_2\text{O})]$$

In other words, it requires 0.26 g. Cu(NO₃)₂.2.5 H₂O per g., of final sorbent to form a 9 wt. % CuO on alumina sorbent where the water pore volume is 83 ml of water per 100 g. of copper oxide on alumina.

In order to prepare the 9 wt. % CuO on alumina, the pores of 91 g. of the alumina are filled with a solution containing 26 g. (0.26 g. of Cu(NO₃)₂.2.5 H₂O/g. sorbent×100 g.) copper nitrate salt dissolved in 75.5 ml. of water to incipient wetness. Slightly more or less liquid solution may be added until the catalyst is uniformly filled with solution. In the case of Cu salts, the color of the filled pellets is light blue and the unfilled pellets remain white. The sorbent is dried in an oven at a temperature sufficient to boil water from the pores without fracturing the sorbent—about 121° C. (250° F.)—for from about 4 to about 8 hours. Then, the temperature is ramped to about 482° C. (900° F.) to decompose the nitrate salt to CuO on the support. Prior to use, the sorbent is stripped with nitrogen in order to avoid contaminating the olefin feed with oxygen.

Preferably, the olefin feedstock is contacted in the liquid phase in a reaction zone with the sorbent of the present invention at effective process conditions to reduce the content of phosphorus-containing compounds in the feedstock, i.e., an effective temperature, pressure, and LHSV (Liquid Hourly Space Velocity). A preferred embodiment of a reactor system for the process is an upflow or downflow fixed bed reactor. An upflow reactor is preferred for better wetting of the sorbent bed. The temperature employed may vary. Although not limited to a particular temperature, best results will be obtained if the process is conducted at temperatures of from about 0° C. to about 100° C., preferably from about 10° C. to about 50° C. The pressures may vary over a range including but not limited to autogeneous pressures and pressures in the range of from about 0.01 MPa to about 50 MPa. A preferred pressure is in the range of from about 0.1 MPa to about 10 MPa. Pressures outside of the stated ranges may be used and are not excluded from the scope of the invention.

The feedstock may flow at a wide range of liquid hourly space velocities (LHSV), defined as liquid feed per hour per volume of sorbent. The LHSV is calculated as follows:

$$\frac{\text{Volume of olefin containing feed}}{\text{Volume of sorbent}} \times \frac{1}{\text{hr}}$$

The lower the LHSV, the greater will be the reduction in content of phosphorus-containing compounds in the feedstock. The LHSV generally is from about 0.01 hr⁻¹ to about 10 hr⁻¹, preferably from about 0.1 hr⁻¹ to about 1 hr⁻¹.

The process is continued for a period of time sufficient to achieve a desired reduction in the content of phosphorus-containing compounds in the olefin stream. The content of phosphorus-containing compounds preferably is reduced to about 1 ppm or less, most preferably to about 0.1 ppm or less. The reaction cycle time may vary from tenths of seconds to a number of hours. The reaction cycle time is largely determined by the reaction temperature, the pressure, the sorbent selected, the liquid hourly space velocity, and the desired reduction in content of phosphorus containing compounds.

At some point, the sorbent becomes saturated, and must be regenerated. SELEXSORB AS™ has an absorptive capacity of about 0.6 grams of phosphorus per gram of sorbent. The sorbent may be regenerated by exposing the sorbent to an oxygen-containing atmosphere at a temperature of from about 200° C. to about 550° C., preferably from about 450° C. to about 600° C. Suitable oxygen containing atmospheres include, but are not necessarily limited to air, oxygen gas, and a combination of oxygen gas with nitrogen gas. A preferred gas is a commercially available combination comprising about 1% oxygen, with the remainder being nitrogen. After exposure to these increased temperatures for a period of time of from about 0.5 hour to about 100 hours, the bed is cooled to at least about 100° C., and preferably to about 25° C., or ambient temperature, in order to avoid overheating upon reuse. The cooled bed is purged with nitrogen or air before reuse in the process. Ten regeneration cycles under these conditions have been shown to produce no loss in sorbent capacity. Some slight loss in sorbent capacity was seen beginning after about 10 regeneration cycles.

Typical olefin feedstocks comprise from about 100 ppm to about 2000 ppm dienes that tend to lower the efficiency of skeletal isomerization catalysts. In a preferred embodiment, the support of the present invention, preferably is a sorbent which sorbs dienes present in initial olefin streams. In a preferred embodiment, the alumina support for copper oxide performs this function. The dienes are sorbed onto the alumina prior to skeletal isomerization. The dienes also may be removed by sorption from the skeletally isomerized product.

$C_6$ to $C_{33}$ olefins have a variety of uses, including but not necessarily limited to uses in paper processing, drilling fluids, and machine or metal working. In a preferred embodiment, the olefin feedstock is converted to branched primary alcohols in the process described in U.S. Pat. No. 5,849,960, incorporated herein by reference. Most preferably, the olefin feedstock is treated before the olefins are fed to a skeletal isomerization catalyst, as described in U.S. Pat. No. 5,849,960. A preferred skeletal isomerization catalyst for use in conjunction with the present invention is a hydrogen ferrierite catalyst, as described in U.S. Pat. No. 5,510,306, incorporated herein by reference.

In a preferred embodiment, the skeletally isomerized olefins are converted to any of a broad range of surfactants, including nonionic, anionic, cationic, and amphoteric surfactants, with a degree of branching of at least 1.0. The skeletally isomerized olefins serve as a surfactant intermediate. Specifically, the skeletally isomerized olefins serve as the hydrophobic moiety of the surfactant molecule, while the moiety added to the olefin during the conversion process serves as the hydrophile.

The invention will be better understood with reference to the following examples, which are illustrative only and not intended to limit the invention to any particular embodiment.

EXAMPLE I

NEODENE 16 containing 20 ppm phosphorus was placed in a jar with SELEXSORB AS™ sorbent crushed to 20×40 mesh and shaken intermittently by a flat bed shaker over a period of 15 hours at 23° C. to achieve equilibration. The NEODENE to SELEXSORB AS™ weight ratios used ranged from 100 to 1000. After equilibration, the NEODENE was separated from the sorbent and analyzed for phosphorus using inductively coupled plasma (ICPO). The results are given in the following Table:

| NEODENE to Sorbent weight ratio | Equilibrium P (ppm) | P loading (g/100 g) |
|---|---|---|
| 100 | 0.5 | 0.16 |
| 200 | 2.2 | 0.36 |
| 150 | 2.5 | 0.26 |
| 250 | 2.6 | 0.43 |
| 350 | 4.9 | 0.52 |
| 450 | 7.8 | 0.54 |
| 550 | 9.7 | 0.56 |
| 1000 | 13.1 | 0.67 |

With an excess of sorbent, phosphorus was reduced to very low levels in the olefin. The capacity of the sorbent also was determined to be about 0.6 grams of phosphorus/100 grams of sorbent.

EXAMPLE II

Phosphorus uptake from NEODENE 16 containing about 20 ppm phosphorus (for 20×40 mesh particles) and 23 ppm phosphorus (for ⅛" spheres) was compared using SELEXSORB AS™ particles having different sizes. The olefin to sorbent weight ratio was 200. The olefin was contacted with the sorbent under the conditions given in Example I for the specified period of time, and then the olefin was separated and analyzed for phosphorus. The results, which are given in the following Table, clearly show that the smaller particles removed phosphorus much more quickly than the larger spheres.

| Contact time (hr) | P in hydrocarbon (ppm) 20 × 40 mesh particles | P in hydrocarbon (ppm) ⅛" spheres |
|---|---|---|
| 0 | 20 | 23 |
| 0.17 | 14.4 | 23 |
| 0.5 | 10.1 | 23 |
| 1 | 7.5 | |
| 2 | 4.3 | |
| 3 | 3.2 | 22 |
| 5 | 2.4 | |
| 7 | 2.2 | 21 |
| 112 | | 10.3 |

EXAMPLE III

One gram of SELEXSORB AS™ (crushed to 20×40 mesh) was equilibrated with 550 grams of NEODENE® containing about 20 ppm phosphorus as described in Example I. The sorbent and the olefin were then separated and the olefin was analyzed to determine the uptake of phosphorus by the sorbent. Following this, the sorbent was regenerated by the following procedure:

a. The sorbent was rinsed with from about 75 to about 100 ml. cyclohexane per gram of sorbent to displace the olefin;

b. The rinsed sorbent was heated under air flow at 125° C. for 6 minutes;

c. The temperature was increased at 3° C./min to 200° C. and held for 2 hours d. The temperature was increased at 2° C./min to 500° C. and held for 2 hours; and e. The regenerated sorbent was cooled in air to ambient temperature.

The regenerated sorbent was contacted with a fresh batch of NEODENE at the same weight ratio of 550 gm NEODENE® to 1 gm sorbent. This procedure was repeated for a total of 14 sorption cycles and 13 regeneration cycles. The capacity of the sorbent for phosphorus after each cycle was calculated and compared to the capacity data for the virgin sorbent. The results are given in the following Table:

| Equilibrium P (ppm) | Virgin Sorbent | Regen 1X | Regen 2X | Regen 3X | Regen 6X | Regen 9X | Regen 12X | Regen 13X |
|---|---|---|---|---|---|---|---|---|
| 0 | 0 | | | | | | | |
| 0.5 | 0.16 | | | | | | | |
| 2.2 | 0.36 | | | | | | | |
| 2.5 | 0.26 | | | | | | | |
| 2.6 | 0.43 | | | | | | | |
| 4.9 | 0.52 | | | | | | | |
| 7.5 | | 0.55 | | | | | | |
| 7.7 | | | | 0.51 | | | | |
| 7.8 | 0.54 | | | | | | | |
| 8.4 | 0.47 | | | | | | | |
| 8.5 | | | 0.46 | | | | | |
| 9.7 | 0.56 | | | | | | | |
| 10.4 | | | | | 0.51 | | | |
| 12.6 | | | | | | | 0.36 | |
| 13.6 | | | | | | 0.6 | | |
| 14.2 | | | | | | | | 0.3 |

After 9 regenerations (10 sorption cycles) the capacity of the sorbent was still comparable to that of the virgin material. However, a decline in capacity was observed after the tenth regeneration.

EXAMPLE IV

A variety of materials were studied as sorbent beds for removing phosphorus impurities. A C16 olefin feed having a density of 0.78 g./cc. and comprising 20.2 ppm phosphorus was fed to a reactor tube having a diameter of 1.73 cm. at a target flow rate of 54 g./hr. The reactor tube was partially filled, to about 50 cm$^3$, with the test sorbent. In this experiment, the test sorbent was SELEXSORB AS™ (1/8" spheres). Samples were taken at various times and the parameters given in the following Table were recorded:

| Elapsed time (hr.) | Product collected (g.) | Fluid flow (g./hr.) | ppm P in fluid coming out of bed |
|---|---|---|---|
| 0 | 0 | | 1.6 |
| 2 | 136.4 | 68.20 | 1.8 |
| 18.5 | 812.5 | 40.98 | 3.4 |
| 25.5 | 1184.7 | 53.17 | 3.9 |
| 42.5 | 2204.5 | 59.99 | 7.3 |
| 49.5 | 2602.7 | 56.89 | 11.1 |
| 66.5 | 3397.1 | 46.73 | 11.6 |
| 73.5 | 3718.4 | 45.90 | 12.1 |
| 90.5 | 3831.8 | 6.67 | 12.5 |
| 96.5 | 4109.8 | 46.33 | 16.1 |
| 116 | 5194.8 | 55.64 | 17.1 |
| 125 | 5534.8 | 37.78 | 17 |

The sorbent removed 50% of the phosphorus from the feedstock for about 60 bed volumes. At the flow conditions of the test, the relatively large spheres of sorbent were not able to lower phosphorus to <0.5 ppm.

EXAMPLE V

A C16 olefin feed having a density of 0.78 g./cc. and comprising 20.2 ppm of phosphorus was fed to a reactor tube having a diameter of 1.73 cm. at a target flow rate of 54 g./hr. The reactor tube was partially filled with the test sorbent. In this experiment, the test sorbent was "AX-200," a trilobe alumina having a particle size of about 1/32". Samples were taken at various times and the following results recorded:

| Elapsed time (hr) | Gm Product Collected | Fluid Flow (gm/hr) | ppm P in fluid coming out of bed |
|---|---|---|---|
| 0 | 0 | | 0.1 |
| 2 | 117.2 | 58.6 | 0.5 |
| 18.5 | 1089.6 | 58.93 | 1.7 |
| 25.5 | 1506.2 | 59.51 | 7.8 |
| 42.5 | 2482. | 57.42 | 17.6 |
| 49.5 | 2833.4 | 50.16 | 22.2 |
| 66.5 | 3730.6 | 52.78 | 29.5 |
| 73.5 | 4018.9 | 41.19 | 28.8 |
| 90.5 | 4115.3 | 5.67 | 23.8 |
| 96.5 | 4421.3 | 51.00 | 23.4 |
| 116 | 5675.3 | 64.31 | 21.9 |
| 125 | 6115.3 | 48.89 | 20.6 |

The small, multilobed particles of sorbent successfully removed substantially all of the phosphorus from the feedstock for about 3 bed volumes, and removed 50% of the phosphorus in the feed for about 40 bed volumes.

EXAMPLE VI

A C16 olefin feed having a density of 0.78 g./cc and comprising 22.6 ppm phosphorus was fed to a reactor tube having a diameter of 1.73 cm at a target flow rate of 30 g./hr. The reactor tube was partially filled, to about 50 cm$^3$, with the test sorbent. The test sorbent was crushed and sieved SELEXSORB AS™ having a particle size of about 14–24 mesh. Samples were taken at various times and the following results recorded:

| Elapsed time (hr.) | Product Collected (g.) | Fluid Flow (g./hr.) | ppm P in fluid coming out of bed |
|---|---|---|---|
| 0 | | | |
| 17.25 | 719.7 | 41.72 | 0.1 |
| 65.25 | 2098.7 | 28.73 | <0.1 |
| 137.75 | 3967.7 | 25.78 | <0.1 |
| 185.75 | 5069.7 | 22.96 | 1.3 |
| 210.25 | 5639.7 | 23.27 | 3.3 |
| 234.25 | 6189.7 | 22.92 | 6.6 |
| 267 | 7003.7 | 24.85 | 10.6 |
| 305.25 | 7993.7 | 25.88 | 11.9 |
| 330.25 | 8630.7 | 25.48 | 14.6 |

The small particles of sorbent successfully removed substantially all of the phosphorus from the feedstock for about 125 bed volumes.

EXAMPLE VII

Example VI was repeated using 9% CuO/AX-300 (1/20" trilobe extrudate). Samples were taken at various times and the following results were recorded:

| Elapsed time (hr) | Gm product Collected | Fluid Flow (gm/hr) | ppm P in fluid coming out of bed |
|---|---|---|---|
| 0 | | | |
| 17.25 | 625.3 | 36.25 | 0.1 |
| 65.25 | 2064.3 | 29.98 | 0 |
| 137.75 | 3752.3 | 23.28 | 0.4 |
| 185.75 | 4810.3 | 22.04 | <0.1 |
| 210.25 | 5375.3 | 23.06 | 3.2 |
| 234.25 | 5951.3 | 24.00 | 6.8 |
| 267 | 6839.3 | 27.11 | 11.6 |
| 305.25 | 7915.3 | 28.13 | 16.9 |
| 330.25 | 8581.3 | 26.64 | 18.9 |

The intermediate sized, multilobed particles of sorbent successfully removed substantially all of the phosphorus from the feedstock for about 130 bed volumes.

EXAMPLE VIII

Example VII was repeated using 18% CuO/AX-300 (1/20" trilobe extrudate). Samples were taken at various times and the following results were recorded:

| Elapsed time (hr.) | Product Collected (g.) | Fluid Flow (g./hr.) | ppm P in fluid coming out of bed |
|---|---|---|---|
| 0 | | | |
| 17.25 | 798.7 | 46.30 | 0.1 |
| 65.25 | 2540.7 | 36.29 | 0.1 |
| 137.75 | 4275.7 | 23.93 | 0.4 |
| 185.75 | 5500.7 | 25.52 | 3.1 |
| 210.25 | 6100.7 | 24.49 | 5.5 |
| 234.25 | 6682.7 | 24.25 | 8.3 |
| 267 | 7600.7 | 28.03 | 13.1 |
| 305.25 | 8680.7 | 28.24 | 17.7 |
| 330.25 | 9410.7 | 29.20 | 19.9 |

The sorbent, which had a size and shape similar to that in Example VII, successfully removed substantially all of the phosphorus from the feedstock for about 130 bed volumes. No additional capacity was observed with the higher metal loading (9 wt. % in Example VII vs. 18 wt. % in Example VIII).

EXAMPLE IX

A C16 olefin feed having a density of 0.78 gm/cc and comprising 10.5 ppm phosphorus was fed to a reactor tube having a diameter of 1.73 cm at a target flow rate of 30 gm/hr. The reactor tube was partially filled with the test sorbent. The test sorbent was 9% CuO/AX200, which has a particle size of about 1/32" trilobe extrudate. Samples were taken at various times and the following results were recorded:

| Elapsed time (hr) | Gm Product Collected | Fluid Flow (gm/hr) | ppm P in fluid coming out of bed |
|---|---|---|---|
| 0 | | | |
| 18.5 | 558.8 | 30.21 | 1 |
| 43 | 1163.8 | 24.69 | <0.1 |
| 139.5 | 2960.8 | 18.62 | 0.1 |
| 163 | 3706.8 | 31.74 | <0.1 |
| 186.75 | 4435.8 | 30.69 | 0.1 |
| 210.75 | 5119.8 | 28.50 | <0.1 |
| 241.25 | 5953.8 | 27.34 | 0.1 |
| 307.5 | 7747.8 | 27.08 | <0.1 |
| 331 | 8469.8 | 30.72 | <0.1 |
| 379.5 | 9924.6 | 30.00 | 0.1 |
| 427 | 11073.6 | 24.19 | 0.3 |
| 474.75 | 12184.6 | 23.27 | 0.6 |
| 523.2 | 13440.6 | 25.90 | 1.3 |

The small, multilobed sorbent successfully removed substantially all of the phosphorus from the feedstock for about 275 bed volumes.

EXAMPLE X

The procedures of Example IX were repeated using 9% CuO on AX-300 (1/20"). The results are given in the following Table:

| Elapsed time (hr) | Gm Product Collected | Fluid Flow (gm/hr) | ppm P in fluid coming out of bed |
|---|---|---|---|
| 0 | | | 0.1 |
| 18.5 | 545.3 | 29.48 | 0 |
| 43 | 1220.3 | 27.55 | 0 |
| 139.5 | 2415.3 | 12.38 | 0.1 |
| 163 | 3036.3 | 26.43 | 0 |
| 186.75 | 3676.3 | 26.95 | 0.1 |
| 210.75 | 4340.3 | 27.67 | 0.1 |
| 241.25 | 5185.3 | 27.70 | 0.2 |
| 307.5 | 6989.3 | 27.23 | 1 |
| 331 | 7743.3 | 32.09 | 1.1 |
| 379.5 | 9127.6 | 28.54 | 1.8 |
| 427 | 10400.6 | 26.80 | 2.6 |
| 474.75 | 11660.6 | 26.39 | 2.8 |
| 523.25 | 12947.6 | 26.54 | |

The intermediate sized, multilobed particles of sorbent successfully removed substantially all of the phosphorus from the feedstock for about 170 bed volumes. The larger size particles produced a lower capacity at the same target flow rate as Example IX using the same phosphorus containing feedstock.

EXAMPLE XI

A series of experiments was performed to demonstrate higher temperature performance (80° C. and 120° C.) using 1/32" trilobe sorbent particles. A C16 olefin feed having a density of 0.78 gm/cc and comprising 20 ppm phosphorus was fed to a reactor tube having a diameter of 1.73 cm$^2$ at a target flow rate of 23 gm/hr. The reactor tube was partially filled with the test sorbent. The test sorbent was 9% CuO/AX300, which has a particle diameter of about 1/32" as a trilobe extrudate. The temperature in the reactor tube was maintained at 80° C. Samples were taken at various times and the following results were recorded:

| Elapsed time (hr) | Gm Product Collected | Fluid Flow (gm/hr) | ppm P in fluid coming out of bed |
|---|---|---|---|
| 0 | | | |
| 3.25 | 76.2 | 23.45 | 0.2 |
| 5.75 | 119.6 | 17.36 | 0.2 |
| 22.5 | 438.3 | 19.03 | 0 |
| 29.5 | 552.1 | 16.26 | 0.1 |
| 45.5 | 665.5 | 7.09 | — |
| 53.5 | 869.5 | 25.50 | 0.1 |
| 71.5 | 1393.8 | 29.13 | 0.1 |
| 80.25 | 1638.3 | 27.94 | 0 |
| 95.75 | 1747.7 | 7.06 | — |
| 103.75 | 1954.3 | 25.83 | 0 |
| 119.75 | 2555.8 | 37.59 | 0 |
| 141.75 | 3322.7 | 34.86 | 0.1 |
| 149.75 | 3565.7 | 30.37 | 0 |
| 165.75 | 4064.2 | 31.16 | 0 |
| 174.5 | 4302.9 | 27.28 | 0 |
| 189.75 | 4747.7 | 29.17 | 0 |
| 197.75 | 4969.4 | 27.71 | 0.1 |
| 213.75 | 5432.6 | 28.95 | 0.2 |
| 237.75 | 6126.3 | 28.90 | 0.7 |
| 244.75 | 6322.5 | 28.03 | 1.2 |
| 264.25 | 6887.7 | 28.98 | 3 |
| 271.5 | 7031.1 | 19.78 | |
| 288.5 | 7032.1 | 0.06 | 10.8 |
| 295.5 | 7342.8 | 44.39 | 5.2 |
| 309.75 | 7837.5 | 34.72 | 7.3 |
| 316.5 | 8059.4 | 32.87 | 10.2 |
| 334 | 8667.1 | 34.73 | |
| 341 | 8908.2 | 34.44 | |

Even at the higher temperature, the sorbent successfully removed substantially all of the phosphorus from the feedstock for about 150 bed volumes.

EXAMPLE XII

The procedures of Example XI were repeated at a temperature of 120° C. The results appear in the following Table:

| Elapsed time (hr) | Gm Product Collected | Fluid Flow (gm/hr) | ppm P in fluid coming out of bed |
|---|---|---|---|
| 0 | | | |
| 3.25 | 103.2 | 0.00 | 0.1 |
| 5.75 | 160 | 22.72 | 0.1 |
| 22.5 | 566.7 | 24.28 | 0.1 |
| 29.5 | 686.5 | 17.11 | 0.1 |
| 45.5 | 788.6 | 6.38 | — |
| 53.5 | 827.1 | 4.81 | 0.1 |
| 71.5 | 1364.7 | 29.87 | 0.4 |
| 80.25 | 1614.7 | 28.57 | 0.4 |
| 95.75 | 1986.5 | 23.99 | 0.3 |
| 103.75 | 2178.4 | 23.99 | 0.3 |
| 119.75 | 2570.1 | 24.48 | 0.3 |
| 141.75 | 3107.9 | 24.45 | 0.3 |
| 149.75 | 3298.4 | 23.81 | 0.2 |
| 165.75 | 3689.4 | 24.44 | 0.3 |
| 174.5 | 3892.1 | 23.17 | 0.2 |
| 189.75 | 4270.7 | 24.83 | 0.3 |
| 197.75 | 4459.8 | 23.64 | 0.2 |
| 213.75 | 4854.5 | 24.67 | 0.3 |
| 237.75 | 5443.7 | 24.55 | 0.6 |
| 244.75 | 5611.2 | 23.93 | 0.9 |
| 264.25 | 6091.1 | 24.61 | 3.8 |
| 271.5 | 6260 | 23.30 | |
| 288.5 | 6683.8 | 24.93 | 10.8 |
| 295.5 | 6848.6 | 23.54 | 13.1 |
| 309.75 | 7193 | 24.17 | 7.3 |
| 316.5 | 7348.4 | 23.02 | 22.2 |
| 334 | 7772.8 | 24.25 | |
| 341 | 7941.6 | 24.11 | |

Again, the higher temperature did not interfere with successful removal of substantially all of the phosphorus from the feedstock for about 140 bed volumes.

EXAMPLE XIII

The procedures of Example I were repeated using different sorbents using a feed containing 18 ppm P and a NEODENE® 16 to solvent weight ratio of 100 with the following results:

| Sorbent | Equilibrium P (ppm) | P loading (g/100 g sorbent) |
|---|---|---|
| BARNABEY SE carbon | 7 | 0.11 |
| BARNABEY CE carbon | 3 | 0.15 |

EXAMPLE XIV

The following examples illustrate the nature of the invention and its impact on skeletal isomerization of detergent range olefins.

A glass column with an inner diameter of 50 mm was packed with 3.2 mm Selexsorb AS spheres obtained from Alcoa Company of America to produce a bed 400 mm in length. 20 liters of NEODENE® 16 olefin, a $C_{16}$ linear, alpha olefin commercially available from Shell Chemical Company, was passed through the packed bed of Selexsorb AS spheres at a weight hourly space velocity of 0.01 per hour and the liquid effluent was collected in a container purged with nitrogen. The phosphorus content of the NEODENE® 16 olefin was reduced from 20 ppm to 0.2 ppm in the process.

EXAMPLE XV

A catalyst was prepared in accordance with Example C of U.S. patent 5,510,306, which has been incorporated herein by reference and is reproduced in part herein for convenience. An ammonium-ferrierite having a molar silica to alumina ratio of 62:1, a surface area of 369 square meters per gram (P/Po=0.03), a soda content of 480 ppm and n-hexane sorption capacity of 7.3 g per 100 g of zeolite was used as the starting zeolite. The catalyst components were mulled using a Lancaster mix muller. The mulled catalyst material was extruded using a 2.25 inch Bonnot pin barrel extruder.

The catalyst was prepared using 1 weight percent acetic acid and 1 weight percent citric acid. The Lancaster mix muller was loaded with 645 grams of ammonium-ferrierite (5.4% LOI) and 91 grams of CATAPAL D® alumina (LOI of 25.7%). The alumina was blended with the ferrierite for 5 minutes during which time 152 milliliters of de-ionized water was added. A mixture of 6.8 grams glacial acetic acid, 7.0 grams of citric acid and 152 milliliters of de-ionized water was added slowly to the muller in order to peptize the alumina. The mixture was mulled for 10 minutes. 0.20 Grams of tetraammine palladium nitrate in 153 grams of de-ionized water were then added slowly as the mixture was mulled for a period of 5 additional minutes. Ten grams of METHOCEL F4M® hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a die plate with 1/16" holes.

The moist extrudates were tray dried in an oven heated to 150° C. 2 hours, and then increased to 175° C. for 4 hours. After drying, the extrudates were broken manually. The extrudates were calcined in flowing air at 500° C. for two hours.

EXAMPLE XVI

Skeletal Isomerization of the NEODENE® 16 olefin was conducted using an olefin isomerization reactor. A stainless steel tube, 25.4 mm OD, 15 mm ID and 685 mm long was used to contain the catalyst. One end of the tube was screwed into a stainless steel head equipped with a thermowell which extended up the center of the tube. The tube was loaded with a small plug of glass wool, then filled to a depth of 150 mm with 20 mesh silicon carbide, and then a small plug of glass wool was added above the SiC. 6.00 grams of the catalyst described in Example XV was admixed with 45 grams of 60–80 mesh SiC and added in three parts to distribute it evenly inside the reactor tube. Another piece of glass wool was added and the remaining volume of the reactor tube was filled with 20 mesh SiC topped by a final piece of glass wool. The tube was screwed into another stainless steel head and a multipoint thermocouple was inserted into the thermowell to allow the temperature above, below and inside the catalyst bed to be monitored. The reactor tube was then installed inside an electric furnace. Connections were made at the top of the reactor to allow nitrogen and the olefin to be passed through the reactor. The bottom of the reactor was connected to a condenser and a product collection system.

Nitrogen at a rate of 6 liters per hour was passed through the reactor while the catalyst bed was heated to 290° C. over a period of 2 hours. NEODENE® 16 olefin prepared by the method of example Example A (with phosphorus content of 0.2 ppm) was pumped to the reactor at a rate of 60.0 grams per hour, allowed to mix with the incoming nitrogen and then passed through the catalyst bed. During the testing the inlet pressure was held at 1.6 psig while the outlet pressure of the reactor was maintained at 1.0 psig. The liquid product was collected in a 5 gallon vessel while the uncondensed gas was passed through a gas meter. Sampling ports incorporated in the reactor allowed the liquid and gas products to be analyzed regularly. The products were analyzed by gas chromatography. The results of the testing are presented in the following Table.

TABLE

The Effect of the Phosphorus Content in NEODENE ® 16 linear alpha olefin on the Degree of Branching During Skeletal Olefin Isomerization

| Olefin Used | Treated NEODENE ® 16 | Untreated NEODENE ® 16 |
|---|---|---|
| Phosphorus Content | 0.2 ppm | 20 ppm |
| Time On Stream, Hr | % Branching In Liquid Product | |
| 13.5 | 97 | 81 |
| 24.5 | 97 | 68 |
| 37.8 | 97 | 56 |
| 64.0 | 97 | 33 |
| 110 | 97 | 20 |
| 230 | 96 | Stopped Test after 110 hours |

In the presence of 20 ppm of phosphorus in the untreated NEODENE®16, the degree of branching declined rapidly with time on stream. In the case of the treated stream, where the phosphorus was reduced to 0.2 ppm, the degree of branching stayed much higher for a much longer time on stream.

EXAMPLE XVII

The procedures of Example I were repeated using a feed containing 20 ppm P, a NEODENE® 16 to sorbent weight ratio of 100, and the following sorbents in place of the SELEXSORB AS™. The results are shown in the following Table:

| Sorbent | Equilibrium P (ppm) | P loading (g/100 g sorbent) |
|---|---|---|
| Ag mordenite (15–20% Ag) | 16 | 0.04 |
| Ag X-zeolite (35% Ag) | <2 | >0.18 |

The procedures of Example I were repeated except the feed contained 16 ppm P. The results are shown in the following Table:

| Sorbent | NEODENE ® to sorbent weight ratio | Equilibrium P (ppm) | P loading (g/100 g sorbent) |
|---|---|---|---|
| Ag mordenite (15–20% Ag) | 100 | 11.2 | 0.05 |
| Ag X-zeolite (35% Ag) | 400 | 6.3 | 0.39 |

In the above Tables, the X-zeolite, which contains larger pores than the mordenite, allows for uptake of a greater amount of the bulky phosphorus containing compounds. Also, the load of Ag on the zeolite was higher, which increased the phosphorus uptake.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process of making a branched primary alcohol composition, comprising:

contacting an olefin feed comprising a content of phosphorus-containing impurities with a sorbent comprising a metal selected from the group consisting of Sc, V, Cr, Fe, Co, Ni, Cu, Zn, Nb, Mn, Ag and combinations thereof under conditions and for a time effective to permit said metal to reduce said content of phosphorus-containing impurities and to produce a purified olefin feed;

contacting said purified olefin feed with a skeletal isomerization catalyst under conditions effective to yield skeletally isomerized olefins; and converting said skeletally isomerized olefins into said primary alcohol composition.

2. A process of making a branched primary alcohol composition, comprising:

contacting an olefin feed comprising a content of phosphorus-containing impurities with a sorbent comprising a metal selected from the group consisting of Fe, Co, Ni, Mn, Ag, and Cu under conditions and for a time effective to permit said metal to reduce said content of phosphorus-containing impurities and to produce a purified olefin feed;

contacting said purified olefin feed with a skeletal isomerization catalyst under conditions effective to yield skeletally isomerized olefins; and converting said skeletally isomerized olefins into said primary alcohol composition.

3. A process of making a branched primary alcohol composition, comprising:

contacting an olefin feed comprising a content of phosphorus-containing impurities with a sorbent comprising a metal selected from the group consisting of copper and silver under conditions and for a time effective to permit said metal to reduce said content of phosphorus-containing impurities and to produce a purified olefin feed;

contacting said purified olefin feed with a skeletal isomerization catalyst under conditions effective to yield skeletally isomerized olefins; and converting said skeletally isomerized olefins into said primary alcohol composition.

4. The process of claim 3 wherein said sorbent further comprises a support, and said support is selected from the group consisting of an acidic alumina and a neutral alumina.

5. The process of claim 2 wherein said sorbent further comprises a support, and said support is selected from the group consisting of an acidic alumina and a neutral alumina.

6. The process of claim 3 wherein said sorbent further comprises a support, and said support is selected from the group consisting of an acidic alumina and a neutral alumina.

7. The process of claim 3 wherein said olefin feed comprises primarily olefins having at least about 6 carbon atoms.

8. The process of claim 2 wherein said olefin feed comprises primarily olefins having at least about 6 carbon atoms.

9. The process of claim 3 wherein said olefin feed comprises primarily olefins having at least about 6 carbon atoms.

10. The process of claim 6 wherein said olefin feed comprises primarily olefins having at least about 6 carbon atoms.

11. The process of claim 3 further comprising regenerating said sorbent.

12. The process of claim 3 further comprising regenerating said sorbent.

13. The process of claim 6 further comprising regenerating said sorbent.

14. The process of claim 11 wherein said regenerating comprises exposing said sorbent to regeneration conditions comprising a quantity of oxygen and a temperature effective to regenerate said sorbent.

15. The process of claim 12 wherein said regenerating comprises exposing said sorbent to regeneration conditions comprising a quantity of oxygen and a temperature effective to regenerate said sorbent.

16. The process of claim 13 wherein said regenerating comprises exposing said sorbent to regeneration conditions comprising a quantity of oxygen and a temperature effective to regenerate said sorbent.

17. A process for purifying an olefin feed comprising a content of phosphorus-containing impurities, said process comprising contacting said olefin feed with a sorbent comprising a metal selected from the group consisting of Sc, V, Cr, Fe, Co, Ni, Cu, Zn, Zr, Nb, Mn, Ag and combinations thereof under conditions and for a time effective to reduce said content of phosphorus-containing impurities and to produce a purified olefin feed.

18. The process of claim 17 wherein said metal is selected from the group consisting of Fe, Co, Ni, Mn, Ag, and Cu.

19. A process for purifying an olefin feed comprising a content of phosphorus-containing compounds, said process comprising contacting said olefin feed with a sorbent comprising an effective amount of a metal selected from the group consisting of copper and silver under conditions and for a time effective to reduce said content of phosphorus-containing compounds and to produce a purified olefin feed, said olefin feed comprising primarily olefins having at least about 6 carbon atoms.

20. The process of claim 17 wherein said sorbent further comprises a support, and said support is selected from the group consisting of an acidic alumina and a neutral alumina.

21. The process of claim 18 wherein said sorbent further comprises a support, and said support is selected from the group consisting of an acidic alumina and a neutral alumina.

22. The process of claim 19 wherein said sorbent further comprises a support, and said support is selected from the group consisting of an acidic alumina and a neutral alumina.

23. The process of claim 17 wherein said olefin feed comprises primarily olefins having at least about 6 carbon atoms.

24. The process of claim 18 wherein said olefin feed comprises primarily olefins having at least about 6 carbon atoms.

25. The process of claim 19 wherein said olefin feed comprises primarily olefins having at least about 6 carbon atoms.

26. The process of claim 20 wherein said olefin feed comprises primarily olefins having at least about 6 carbon atoms.

27. The process of claim 21 wherein said olefin feed comprises primarily olefins having at least about 6 carbon atoms.

28. The process of claim 22 wherein said olefin feed comprises primarily olefins having at least about 6 carbon atoms.

29. The process of claim 17 further comprising regenerating said sorbent.

30. The process of claim 18 further comprising regenerating said sorbent.

31. The process of claim 19 further comprising regenerating said sorbent.

32. The process of claim 20 further comprising regenerating said sorbent.

33. The process of claim 21 further comprising regenerating said sorbent.

34. The process of claim 22 further comprising regenerating said sorbent.

35. The process of claim 29 wherein said regenerating comprises exposing said sorbent to regeneration conditions comprising a quantity of oxygen and a temperature effective to regenerate said sorbent.

36. The process of claim 30 wherein said regenerating comprises exposing said sorbent to regeneration conditions comprising a quantity of oxygen and a temperature effective to regenerate said sorbent.

37. The process of claim 31 wherein said regenerating comprises exposing said sorbent to regeneration conditions comprising a quantity of oxygen and a temperature effective to regenerate said sorbent.

38. The process of claim 3 wherein said converting comprises hydroformylating said skeletally isomerized olefin.

39. The process of claim 2 wherein said converting comprises hydroformylating said skeletally isomerized olefin.

40. The process of claim 3 wherein said converting comprises hydroformylating said skeletally isomerized olefin.

41. The process of claim 3 wherein said purified olefin feed consists of about 0.5 ppm or less of said phosphorus-containing compounds.

42. The process of claim 3 wherein said purified olefin feed consists of about 0.5 ppm or less of said phosphorus-containing compounds.

43. The process of claim 6 wherein said purified olefin feed consists of about 0.5 ppm or less of said phosphorus-containing compounds.

44. The process of claim 17 wherein said purified olefin feed consists of about 0.5 ppm or less of said phosphorus-containing compounds.

45. The process of claim 18 wherein said purified olefin feed consists of about 0.5 ppm or less of said phosphorus-containing compounds.

46. The process of claim 19 wherein said purified olefin feed consists of about 0.5 ppm or less of said phosphorus-containing compounds.

47. The process of claim 20 wherein said purified olefin feed consists of about 0.5 ppm or less of said phosphorus-containing compounds.

48. The process of claim 21 wherein said purified olefin feed consists of about 0.5 ppm or less of said phosphorus-containing compounds.

49. The process of claim 22 wherein said purified olefin feed consists of about 0.5 ppm or less of said phosphorus-containing compounds.

50. The process of claim 23 wherein said purified olefin feed consists of about 0.5 ppm or less of said phosphorus-containing compounds.

51. The process of claim 24 wherein said purified olefin feed consists of about 0.5 ppm or less of said phosphorus-containing compounds.

52. The process of claim 25 wherein said purified olefin feed consists of about 0.5 ppm or less of said phosphorus-containing compounds.

* * * * *